(12) United States Patent
Ruh et al.

(10) Patent No.: US 10,537,284 B1
(45) Date of Patent: Jan. 21, 2020

(54) ENHANCED SENSOR SIGNAL COLLECTION AND REFLECTION OF REFLECTED AND/OR SCATTERED LIGHT

(71) Applicant: Apple Inc., Cupertino, CA (US)

(72) Inventors: Richard Ruh, Monte Sereno, CA (US); Ueyn L. Block, Menlo Park, CA (US); Guocheng Shao, San Jose, CA (US)

(73) Assignee: Apple Inc., Cupertino, CA (US)

( * ) Notice: Subject to any disclaimer, the term of this patent is extended or adjusted under 35 U.S.C. 154(b) by 270 days.

(21) Appl. No.: 15/253,529

(22) Filed: Aug. 31, 2016

Related U.S. Application Data

(60) Provisional application No. 62/235,236, filed on Sep. 30, 2015.

(51) Int. Cl.
| | | |
|---|---|---|
| *A61B 5/024* | (2006.01) | |
| *A61B 5/00* | (2006.01) | |
| *G02B 5/136* | (2006.01) | |
| *G02B 5/124* | (2006.01) | |
| *A61B 5/1455* | (2006.01) | |

(Continued)

(52) U.S. Cl.
CPC .......... *A61B 5/681* (2013.01); *A61B 5/14552* (2013.01); *A61B 5/6844* (2013.01); *G01J 1/0233* (2013.01); *G01J 1/44* (2013.01); *G02B 5/124* (2013.01); *G02B 5/136* (2013.01); *A61B 2562/0238* (2013.01); *A61B 2562/0257* (2013.01); *A61B 2562/066* (2013.01); *A61B 2562/12* (2013.01)

(58) Field of Classification Search
CPC ........... A61B 5/024; A61B 5/00; A61B 5/026; A61B 5/0295; A61B 5/1455; A61B 5/02427; A61B 5/7264; A61B 5/6898; A61B 5/681; A61B 5/14551; A61B 5/0261; A61B 5/02438; A61B 5/0013; A61B 2562/0233
See application file for complete search history.

(56) References Cited

U.S. PATENT DOCUMENTS

| | | |
|---|---|---|
| 5,483,261 A | 1/1996 | Yasutake |
| 5,488,204 A | 1/1996 | Mead et al. |

(Continued)

FOREIGN PATENT DOCUMENTS

| | | |
|---|---|---|
| JP | 2000-163031 A | 6/2000 |
| JP | 2002-342033 A | 11/2002 |

(Continued)

OTHER PUBLICATIONS

International Search Report dated Nov. 6, 2015, for PCT Application No. PCT/US2015/042982, filed Jul. 30, 2015, five pages.

(Continued)

*Primary Examiner* — Carl H Layno
*Assistant Examiner* — Jon Eric C Morales
(74) *Attorney, Agent, or Firm* — Brownstein Hyatt Farber Schreck, LLP

(57) ABSTRACT

The present disclosure relates generally to electronic devices and methods for sensor signal collection. The electronic devices may include retroreflectors for redirecting scattered light back to the photodetector. The retroreflectors may be positioned at various locations on or in the electronic device, and may employ various geometric elements having retroreflective capability.

20 Claims, 7 Drawing Sheets

(51) Int. Cl.
*G01J 1/44* (2006.01)
*G01J 1/02* (2006.01)

(56) References Cited

U.S. PATENT DOCUMENTS

| | | |
|---|---|---|
| 5,759,156 A | 6/1998 | Hayakawa et al. |
| 5,825,352 A | 10/1998 | Bisset et al. |
| 5,835,079 A | 11/1998 | Shieh |
| 5,880,411 A | 3/1999 | Gillespie et al. |
| 6,188,391 B1 | 2/2001 | Seely et al. |
| 6,277,067 B1 | 8/2001 | Blair |
| 6,310,610 B1 | 10/2001 | Beaton et al. |
| 6,323,846 B1 | 11/2001 | Westerman et al. |
| 6,533,729 B1 | 3/2003 | Khair et al. |
| 6,690,387 B2 | 2/2004 | Zimmerman et al. |
| 7,015,894 B2 | 3/2006 | Morohoshi |
| 7,139,076 B1 | 11/2006 | Marbach |
| 7,184,064 B2 | 2/2007 | Zimmerman et al. |
| 7,450,799 B2 | 11/2008 | Selbrede et al. |
| 7,616,110 B2 | 11/2009 | Crump et al. |
| 7,643,153 B2 | 1/2010 | de Boer et al. |
| 7,663,607 B2 | 2/2010 | Hotelling et al. |
| 7,729,748 B2 | 6/2010 | Florian |
| 8,252,369 B2 | 8/2012 | Jiang |
| 8,378,811 B2 | 2/2013 | Crump et al. |
| 8,479,122 B2 | 7/2013 | Hotelling et al. |
| 8,618,930 B2 | 12/2013 | Papadopoulos et al. |
| 10,092,197 B2 | 10/2018 | Han |
| 2002/0151775 A1 | 10/2002 | Kondo |
| 2004/0032728 A1 | 2/2004 | Galli |
| 2005/0075549 A1 | 4/2005 | Kondoh et al. |
| 2006/0197753 A1 | 9/2006 | Hotelling |
| 2008/0097221 A1 | 4/2008 | Florian |
| 2008/0228089 A1 | 9/2008 | Cho et al. |
| 2009/0018452 A1 | 1/2009 | Sugiura et al. |
| 2013/0123591 A1 | 5/2013 | Naganuma et al. |
| 2013/0207851 A1 | 8/2013 | Dabov |
| 2014/0121471 A1 | 5/2014 | Walker |
| 2014/0127996 A1 | 5/2014 | Park et al. |
| 2014/0142403 A1 | 5/2014 | Brumback et al. |
| 2014/0155705 A1 | 6/2014 | Papadopoulos et al. |
| 2014/0275852 A1 | 9/2014 | Hong et al. |
| 2014/0361147 A1 | 12/2014 | Fei |
| 2014/0378844 A1 | 12/2014 | Fei |
| 2015/0234188 A1* | 8/2015 | Lee .................. G02B 27/0172 345/633 |
| 2016/0058309 A1 | 3/2016 | Han |
| 2016/0058313 A1 | 3/2016 | Sato |
| 2016/0327921 A1 | 11/2016 | Ribbich et al. |
| 2019/0000331 A1 | 1/2019 | Han |

FOREIGN PATENT DOCUMENTS

| | | |
|---|---|---|
| WO | WO-2014/043410 A1 | 3/2014 |
| WO | WO-2016/032682 A1 | 3/2016 |

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Non-Final Office Action dated Mar. 28, 2016, for U.S. Appl. No. 14/470,834, filed Aug. 27, 2014, 13 pages.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Spigulis, J. et al. (Apr. 25, 2008). "Wearable wireless photoplethysmography Sensors," Institute of Atomic Physics and Spectroscopy, University of Latvia, Proc. of SPIE, vol. 6991, pp. 699120-699120-7, XP055223673.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

Non-Final Office Action dated Jun. 13, 2017, for U.S. Appl. No. 14/470,834, filed Aug. 27, 2014, 15 pages.

Final Office Action dated Jan. 11, 2018, for U.S. Appl. No. 14/470,834, filed Aug. 27, 2014, 16 pages.

Notice of Allowance dated May 25, 2018, for U.S. Appl. No. 14/470,834, filed Aug. 27, 2014, nine pages.

Final Office Action dated Dec. 7, 2016, for U.S. Appl. No. 14/470,834, filed Aug. 27, 2014, 15 pages.

* cited by examiner

ENHANCED SENSOR SIGNAL COLLECTION AND REFLECTION OF REFLECTED AND/OR SCATTERED LIGHT

CROSS-REFERENCE TO RELATED APPLICATIONS

This application claims priority to U.S. Provisional Patent Application Ser. No. 62/235,236, filed Sep. 30, 2015, which is hereby incorporated by reference in its entirety.

FIELD

The present disclosure relates generally to electronic devices and methods for sensor signal collection. The electronic devices may include a retroreflector for redirecting reflected and/or scattered light back out of the device to a body surface. The retroreflector may be positioned at various locations within the electronic device, and may employ various geometric elements having retroreflective capability.

BACKGROUND

Sensors for measuring various types of signals, including physiological signals, often illuminate an individual's tissue with light from a light source and then measure the light that is reflected back onto a detector. For example, photoplethysmographic (PPG) sensors may consist of infrared or green light-emitting diodes (LEDs) and photodetectors for measuring heart rate, oxygen saturation ($SpO_2$), etc. However, the interaction of light with biological tissue such as skin and/or the structure of the sensor itself can be quite complex and typically involves scattering. In other words, not all of the emitted light is reflected toward the photodetector, but is scattered in other non-useful directions after exiting the skin. Metallic surfaces can be used to reflect and/or redirect light to improve sensor performance, but the addition of metallic surfaces can also interfere with electromagnetic and capacitive signal detection. Accordingly, electronic devices having means and methods for collecting and redirecting reflected and/or scattered light may beneficial.

SUMMARY

Disclosed herein are electronic devices and methods for sensor signal collection, e.g., PPG signal collection. The electronic devices may include a retroreflector capable of redirecting reflected and/or scattered light out of the device toward body tissue and configured to minimize light scattering. As used herein, the term "retroreflector" refers to a component capable of reflecting light back along a direction that is parallel or nearly parallel to but opposite in direction from the light source irrespective of the angle of incidence. The retroreflector may be implemented as a component of a sensor system (e.g., a PPG sensor system or a proximity sensor system) or provided as another part of the electronic device (e.g., a portion or surface of the electronic device housing). It may be useful to include the retroreflectors in wristwatch devices that measure physiological signals to obtain various types of biometric information.

The electronic devices for sensor signal collection generally include a housing having a back surface (e.g., back crystal) and a light emitter unit and a photodetector within the housing. The light emitter unit can comprise a light emitter and one or more retroreflectors, where a retroreflector can comprise a substrate having a reflective surface configured to redirect reflected and/or scattered light out of the housing. The retroreflector may redirect the reflected and/or scattered light to a body tissue for potential reflection to a photodetector. In some instances, it may beneficial to provide the retroreflector adjacent to the light emitter within the same cavity. In other instances, the retroreflector may be disposed within a surface (e.g., back crystal) of the housing. The back surface may also include one or more windows within which the retroreflector may be disposed on or adjacent to. The electronic device may include any suitable number of retroreflectors, and these retroreflectors can be configured in any suitable manner within the housing. For example, when two retroreflectors are employed, one can be provided adjacent to the light emitter, and the other within the back surface of the housing.

The reflective surface of the retroreflector may be configured in various ways on the substrate. For example, the reflective surface may be disposed on the outer surface of the substrate, on a portion (e.g., a discrete portion) of the substrate, or in a pattern on the substrate. Patterning may include, e.g., providing the reflective surface on a perimeter or central area of the substrate, in one or more strips on the substrate, or symmetrically or asymmetrically on the substrate. In some instances, the reflective surface comprises a coating on the substrate. The substrate may be a lens or comprise a material that allows transmission of light.

The reflective surface may include a geometric element. The geometric element may comprise various shapes and geometric configurations, so long as they are suitable for redirecting reflected and/or scattered light in a retroreflective manner. For example, the geometric element may comprise a component structured as a corner cube, a cat's eye, a sphere or hemisphere, a prism, or a combination thereof. The geometric element may be integrally formed (e.g., by molding, embossing, or mechanical machining) on the inner or the outer surface of the substrate. Alternatively, the geometric element may be provided in a coating that is layered onto the substrate.

Methods for sensor signal collection are also disclosed herein. The methods generally include the steps of attaching a electronic device to a body area of a user, the electronic device comprising a housing having a back surface; and a light emitter unit and a photodetector within the housing, the light emitter unit comprising a light emitter and a retroreflector, where the retroreflector comprises a substrate having a reflective surface; illuminating the body area with light from the light emitter; and redirecting reflected and/or scattered light out of the housing using the retroreflector. The retroreflector may redirect the reflected and/or scattered light to a body tissue for potential reflection to a photodetector. For example, when the electronic device is a wristwatch, the retroreflector may redirect reflected and/or scattered light to the wrist of a user. The reflective surface may be disposed on any suitable surface of the substrate and comprise a coating and/or geometric elements, as previously stated.

One useful electronic device including a retroreflector for signal collection comprises a wristwatch. The watch can be used to measure and/or monitor various physiological parameters, e.g., heart rate, oxygen saturation, etc., or measure proximity to a body area. Enhancing the collection of light may help to improve detection of physiological signals, improve generation of proximity curves, as well as save battery life of the electronic device.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise.

It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

DESCRIPTION OF THE FIGURES

For a better understanding of the various described embodiments, reference should be made to the Detailed Description below, in conjunction with the following drawings in which like reference numerals refer to corresponding parts throughout the figures.

DETAILED DESCRIPTION

The following description sets forth exemplary electronic devices and methods for signal collection, e.g., physiological signal collection. It should be recognized, however, that such description is not intended as a limitation on the scope of the present disclosure but is instead provided as a description of exemplary embodiments.

The electronic devices described herein may include retroreflectors for redirecting reflected and/or scattered light out of the device. The retroreflectors may be positioned at various locations on or within the electronic device, and may employ various geometric elements having retroreflective capability. Although the electronic devices are primarily described as including retroreflectors, it is understood that in some instances, additional or alternative types of reflectors, such as specular reflectors or diffuse reflectors, may be employed.

Figure 6:
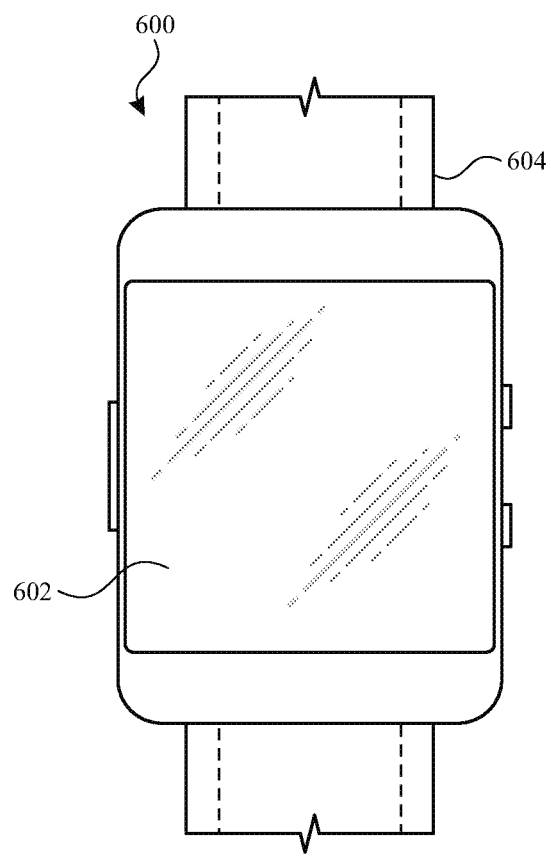
FIG. 6 illustrates an exemplary wristwatch that may employ a retroreflector.

The electronic devices may be any electronic device suitable for contact with or located within close proximity to a user's skin, e.g., a phone, wristwatch, arm or wristband, headband, or any device where collection of signals (physiological signals) may be useful. The electronic device may be worn on a wrist, ankle, head, chest, leg, etc., with the use of an attachment mechanism that may be flexible and/or capable of adjustably fitting a user. For example, the attachment mechanism may be a band made from a flexible material or band that may be secured to the user through the use of hooks and loops (e.g., Velcro), a clasp, and/or a band having memory of its shape, e.g., through the use of a spring metal band. Other exemplary attachment mechanisms include watchstraps, belts, and so forth. These attachment mechanisms may permit the device to be worn by a user. In one variation, as shown in FIG. 6, the electronic device is a wristwatch 600 that includes a housing 602 in which the retroreflector may be disposed and a watchband 604.

In general, the electronic devices comprise a housing having a back surface; and a light emitter unit and a photodetector within the housing. The light emitter unit can comprise a light emitter and a retroreflector, where the retroreflector can include a substrate having a reflective surface configured to redirect reflected and/or scattered light out of the housing. Additionally, the electronic devices may include a processor within the housing configured to run an algorithm with the signals, e.g., PPG signals or proximity related signals, collected from the photodetector to obtain a physiological parameter such as heart rate, oxygen saturation, etc., or distance/proximity measurements.

The housing of the electronic devices may be configured to have any size and shape suitable for the body area of contact, and may include a housing comprising an upper surface, a back surface (opposite the upper surface, where display 406 can be located), and side surfaces, an interior enclosed within the surfaces, and a display 406 that can be mounted in the upper surface of the housing. The display may, for example, be a touch screen or may be a display that is not touch sensitive. The display may include image pixels formed from light-emitting diodes (LEDs), organic LEDs (OLEDs), plasma cells, electrowetting pixels, electrophoretic pixels, liquid crystal display (LCD) components, or other suitable image pixel structures. A display cover layer such as a layer of cover glass or a transparent plastic layer may cover the surface of display. The display cover layer may have one or more openings. Windows may be provided in the display cover layer to allow light to pass through the display cover layer in connection with the operation of a light sensor, camera, or other optical component.

The housing, which may sometimes be referred to as a case, may be formed of plastic, glass, ceramics, fiber composites, metal (e.g., stainless steel, aluminum, etc.), other suitable materials, or a combination of these materials. In some variations, the housing or parts thereof may be formed from dielectric or other low-conductivity material. In other variations, the housing or at least some of the structures that make up the housing may be formed from metal elements. The housing material is generally an opaque material that blocks light transmission. In some instances, the back surface of the housing can comprise a crystal material (e.g., back crystal) having windows through which light may be emitted and detected.

The interior of the housing may comprise a sensor system capable of obtaining signals (e.g., PPG signals relating to a physiological parameter, or signals relating to body/tissue proximity). The sensor system may include one or more light emitters and one or more photodetectors. Exemplary light emitters can include, without limitation, light emitting diodes (LEDs), lasers, incandescent lights, and fluorescent lights. The LED may be a green LED, red LED, or an infrared (IR) LED. When more than one light emitter is used, the plurality can include the same or different light emitters (with different emission/illumination wavelengths). For example, a combination of one or more green LEDs and IR LEDs may be used. With respect to the photodetector, any suitable photodetector may be employed. Exemplary photodetectors may comprise a semiconductor, image pixels, optical detectors, etc.

Any suitable number of light emitters and photodetectors can be provided on or within the electronic device. For example, the electronic device may include a single light emitter and a plurality of photodetectors. In another variation, the proximity sensor comprises a plurality of light emitters and a single photodetector. Some variations of the proximity sensor may include a plurality of light emitters and a plurality of photodetectors. The light emitters and photodetectors may also be arranged in any suitable configuration on or within the electronic device. For example, they can be symmetrically or asymmetrically arranged on or within the electronic device.

A plurality of openings or windows may be provided in the back surface of the housing, and configured for transmission and reflection of light there through. The housing may include any suitable number of windows. The windows may be of any suitable dimension that allows the transmission and reflection of light for obtaining signals.

The light emitter unit of the electronic devices disclosed herein generally includes a light emitter and a retroreflector that is structured to redirect reflected and/or scattered light in a useful direction, e.g., out of the device housing toward body tissue and potentially to the photodetector. It may be useful to employ a retroreflector when there is a small distance between a light emitter and a photodetector of a sensor system. The retroreflector can include a substrate having a reflective surface. In some variations, the reflective surface is disposed on an outer surface of the substrate. In other variations, the reflective surface is disposed on a portion of the substrate, or configured as a pattern on the substrate. For example, patterning may include placing the reflective surface on a discrete portion(s) of the substrate. Patterning may further include, e.g., providing the reflective surface on a perimeter or central area of the substrate, in one or more strips on the substrate, or symmetrically or asymmetrically on the substrate. Alternatively, the reflective surface may comprise a coating on the substrate.

The reflective surface may comprise a geometric element having retroreflective capability. The geometric element may have any suitable structure (e.g., geometric structure) that can allow redirection or reflection of reflected and/or scattered light in a retroreflective manner (e.g., along a vector parallel (or nearly parallel) to, but opposite in direction from the incident (scattered) light). One of skilled in the art would understand that nearly parallel includes, for example, a 5-10% deviation from parallel. Exemplary geometric elements can include, without limitation, corner cubes, cat's eye structures, hemispheric structures, prisms, and combinations thereof.

The substrate of the retroreflectors may be transparent. In one variation, the substrate is a component used within the housing windows to protect elements within the housing from the external environment. In other variations, the substrate comprises an optical article. The optical article may be a lens, e.g., a Fresnel lens or other type of lens. In some instances, e.g., when the substrate is placed within the windows in the back surface of the housing, any geometric element(s) disposed on the substrate may obscure the view into the housing, and thus may be cosmetically useful.

The substrate of the retroreflector may comprise various types of materials. Exemplary substrate materials can include, without limitation, glass, crystal, and polymeric materials. The polymeric materials can include without limitation, thermoplastic materials such as polycarbonates and thermoplastic polyurethanes or thermosetting (cross-linked) materials such as those obtained by polymerization of allyl derivatives such as the allyl carbonates of linear or branched aliphatic or aromatic polyols, such as ethylene glycol bis(allyl carbonate), diethylene glycol bis(2-methyl carbonate), diethylene glycol bis(allyl carbonate), ethylene glycol bis(2-chloroallyl carbonate), triethylene glycol bis (allyl carbonate), 1,3-propanediol bis(allyl carbonate), propylene glycol bis(2-ethylallyl carbonate), 1,3-butenediol bis (allyl carbonate), 1,4-butenediol bis(2-bromoallyl carbonate), dipropylene glycol bis(allyl carbonate), trimethylene glycol bis(2-ethylallyl carbonate), pentamethylene glycol bis(allyl carbonate), isopropylene bisphenol-A bis (allyl carbonate); poly(meth)acrylates and copolymer based substrates, such as substrates obtained by the polymerization of alkyl methacrylates, in particular C1-C4 alkyl methacrylates such as methyl(meth)acrylate and ethyl(meth)acrylate, substrates comprising (meth)acrylic polymers and copolymers derived from bisphenol-A, polyethoxylated aromatic (meth)acrylates such as the polyethoxylated bisphenolate di(meth)acrylates, polythio(meth)acrylates; polyurethanes, polythiourethanes; polyepoxides; polyepisulfides; as well as copolymers thereof and blends thereof. In some variations, the substrate comprises a thermoplastic resin. In other variations, the substrate comprises an epoxy resin.

The substrate can include an inner surface and an outer surface. These surfaces may be flat, concave, or convex. The reflective surface can be disposed on the outer surface of the substrate, but may be disposed on the inner surface, if desired. When the reflective surface comprises geometric elements, they can be integrally formed on a surface of the substrate. For example, the geometric elements can be integrally molded, embossed, or otherwise mechanically fashioned on the surface of the substrate.

Alternatively, the reflective surface can be included a coating that is layered onto the substrate. When the reflective surface comprises geometric elements, they can be molded using an adhesive polymeric material (e.g., a pressure sensitive adhesive), a thermoplastic polymer, or any one of the materials disclosed above, or embossed on a blank polymeric sheet, etc., and then attached to a surface of the substrate. Exemplary pressure sensitive adhesives comprise rubbers, vinyl ethers, acrylics, styrene block copolymers, silicones, and nitriles. Exemplary thermoplastic polymers include without limitation, polyethylene, polyvinylchloride, polypropylene, and polystyrene. When the coating is not formed from a pressure sensitive adhesive, it may be attached to the substrate using any suitable adhesive, e.g., a liquid glue or curable adhesive comprising a polyurethane compound, an epoxy compound, and/or a (meth)acrylate compound.

The geometric elements may be disposed on the substrate in any suitable fashion that enables enhanced collection of light. The geometric elements may comprise corner cubes, cat's eye structures, hemispheric structures, prisms, or combinations thereof, as previously stated. Whether integrally formed on a surface of the substrate or layered in a coating thereon, the geometric elements may be disposed on the entire inner surface or entire outer surface of the substrate, disposed on a portion of the inner surface or on a portion of the outer surface of the substrate, or configured as a pattern on the inner surface or on the outer surface of the substrate. For example, patterning may include placing the geometric elements on a discrete portion(s) of the inner surface or on a discrete portion(s) of the outer surface of the substrate. Patterning may further include, e.g., providing the geometric elements on a perimeter or central area of the substrate, in one or more strips on the substrate, or symmetrically or asymmetrically on the substrate. In some variations, the same geometric element is disposed on the substrate. In other variations, different or combinations of geometric elements are disposed on the substrate.

The retroreflector may be positioned in any suitable location on or within the electronic device that enables enhanced collection of light. In one variation, the retroreflector can be disposed within the interior of the housing (e.g., inside the cavity including the light emitter) adjacent the light emitter. In another variation, the retroreflector can be disposed on the exterior of the housing. In yet a further variation, the retroreflector can be disposed within the back surface of the housing (e.g., within one or more windows in the back surface of the housing).

Figure 1A:
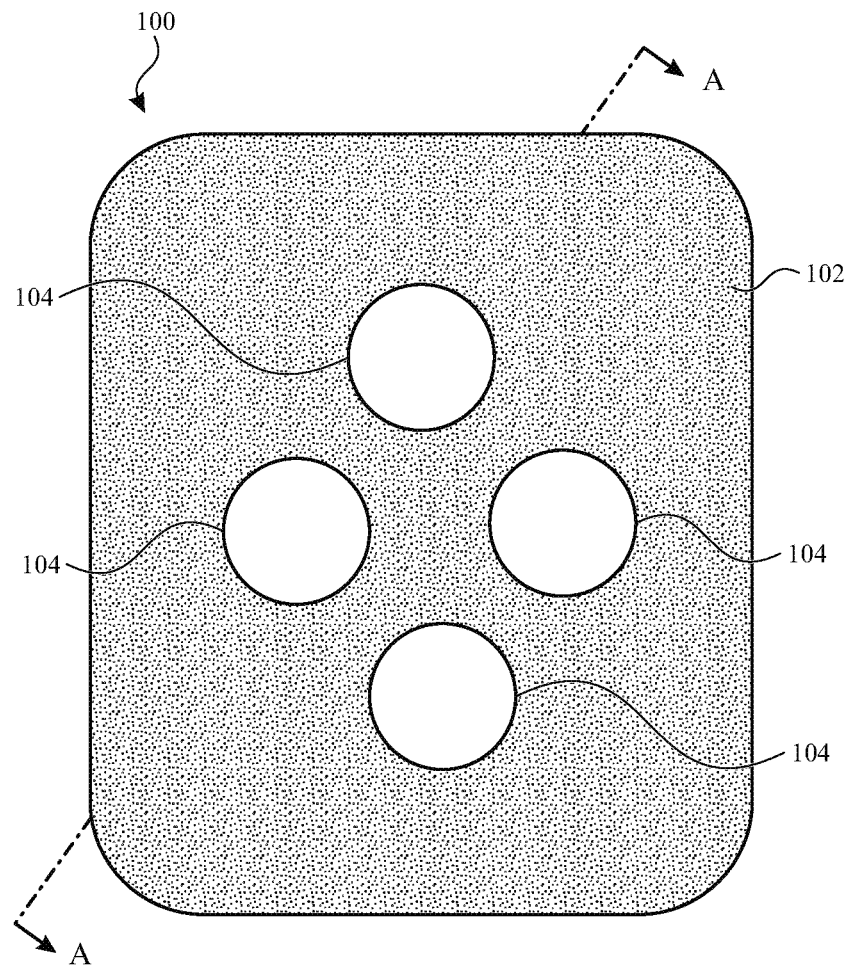
FIG. 1A illustrates an exemplary electronic device including a plurality of windows in the back surface of the device housing according to examples of the disclosure.

For example, as shown in FIG. 1A, the lower surface 102 of an electronic device housing 100 can include four openings or windows 104. As shown in the cross-sectional view of the housing 100 taken along line A-A, and provided in FIG. 1B, a retroreflector 106 can be positioned near LED 108 within cavity 110. The retroreflector 106 may be any one of the retroreflectors previously described above. Light 112A emitted from LED 108 can travel through window 104 to illuminate body tissue 114 and can reflect back in the direction of arrow 112B through another window 104 toward photodetector 116. In some instances, some of the emitted light from LED 108 may enter tissue 114, but may not reflect back toward photodetector 116. By having retroreflector 106 positioned within cavity 106 near or adjacent to LED 108, reflected and/or scattered light (e.g., light 118) can be reflected back into the tissue 114 in the direction of arrow 120 and can be potentially reflected to photodetector 116. In this manner, enhanced collection of light can be accomplished. Although shown as being adjacent the LED, it is understood that the retroreflector can be positioned in any suitable location that enables the enhanced collection of light. In some instances, multiple retroreflectors are employed, e.g., within the housing or a back surface thereof, or on an exterior surface of the housing.

In some examples, retroreflectors can be located in multiple locations within cavity 110. FIG. 1C illustrates an exemplary electronic device including multiple retroreflectors located within the light emitter cavity according to examples of the disclosure. In some instances, some light emitted by LED 108 may not exit housing 100 through window 104, and instead, can be reach housing 100 and be absorbed by it. For example, light 112C emitted from LED 108 may be reach housing 100 instead of exiting window 104. When light is absorbed by housing 100 or may be lost (e.g., due to being trapped within cavity 110), the intensity of LED 108 may need to be increased for photodetector 116 to be able to collect enough light for an accurate signal measurement. Increases in LED 108 intensity may require higher power consumption, which may be undesirable for compact, portable electronic devices.

To enhance collection of light by photodetector 116, housing 100 can be configured with a plurality of retroreflectors 106. Plurality of retroreflectors can be located in one or more locations, such as on the top surface (e.g., opposite to window 104), side surfaces, and/or bottom surface (e.g., on the same plane as window 104) of housing.

Examples of the disclosure can include utilizing other types of reflectors (e.g., Lambertian reflectors) for light reflection. FIG. 1D illustrates an exemplary electronic device including retroreflectors and Lambertian reflectors according to examples of the disclosure. In some instances, light that has interacted with tissue 114 can reflect back through window 104 and can enter cavity 111. In some instances, light 112D may not be incident on the surface of photodetector 116, and instead, may be reach housing 100. Light 112D may be absorbed by housing 100 or may be lost (e.g., due to being trapped in cavity 111). Absorbed or lost light may lead to low signal intensity, which can require increases in LED 108 intensity and/or can lead to inaccurate measurements.

In some examples, cavity 111 can include one or more reflectors 107. Reflectors 107 can be non-retroreflectors configured to reflect light, shown by arrow 112E, back towards photodetector 116. In some examples, the housing can be configured with a plurality of cavities (e.g., cavity 110 and cavity 111), where at least two cavities can include different types of reflectors. For example, cavity 110 can include one or more retroreflectors 106 configured to reflect light emitted by LED 108 back along a direction (e.g., in the same direction as light 112A) that is parallel (or nearly parallel) to, but opposite from the direction of the light source, irrespective of the angle of incidence. One of skilled in the art would understand that nearly parallel includes, for example, a 5-10% deviation from parallel. Cavity 111 can include Lambertian reflectors configured to reflect light back in any, some, or all directions.

Figure 2:
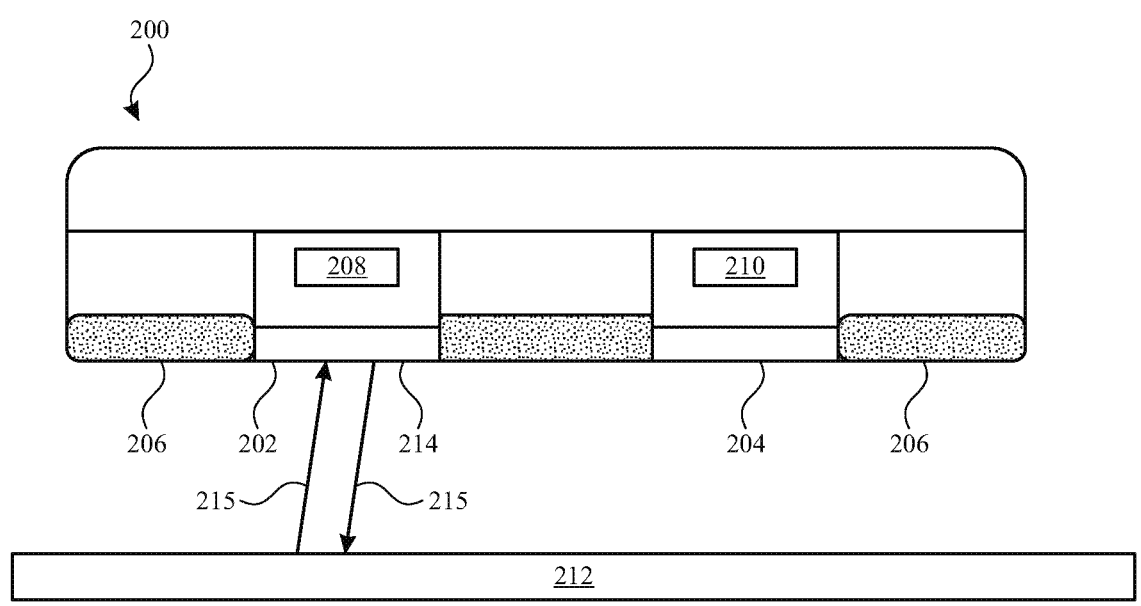
FIG. 2 illustrates a cross-sectional view of the electronic device housing comprising a retroreflector within a window of the housing according to examples of the disclosure.

The retroreflector may also be positioned within one or more windows disposed in the back surface of an electronic device housing. FIG. 2 illustrates a cross-sectional view of an exemplary housing including a window with a retroreflector according to examples of the disclosure. Housing 200 can include window 202 coupled to cavity 220 and window 204 coupled to cavity 221, where both windows can be included in back surface 206. Cavity 220 can include light emitter 208, and cavity 221 can include photodetector 210. Housing 200 and back surface 206 can include an opaque material configured to block the transmission of light. Window 202 can be located near light emitter 208, and window 204 can be located near photodetector 210. Light 215a emitted by light emitter 208 can pass through window 202 and can travel toward body tissue 212. In some instances, light 215a can interact with tissue 212 and can reflected back into cavity 221 to be collected by photodetector 210.

In some instances, light 215a can reflect back towards cavity 220 as light 215b. Light 215b may enter cavity 220 and can become absorbed by housing 200 and/or lost. Disposed within the window 202 can be substrate 214 comprising retroreflective geometric elements. As illustrated in the figure, these retroreflective geometric elements can be capable of reflecting and/or redirecting reflected and/or scattered light, such as light 215c back to tissue 212, and subsequently to photodetector 210. In this manner, another mode of enhanced collection of light may be achieved. In some examples, back surface 206 can include one or more retroreflectors at one or more locations (e.g., between edge of housing 200 and window 202, between window 202 and window 204, between window 204 and edge of housing 200, and/or a combination thereof).

Figure 3:
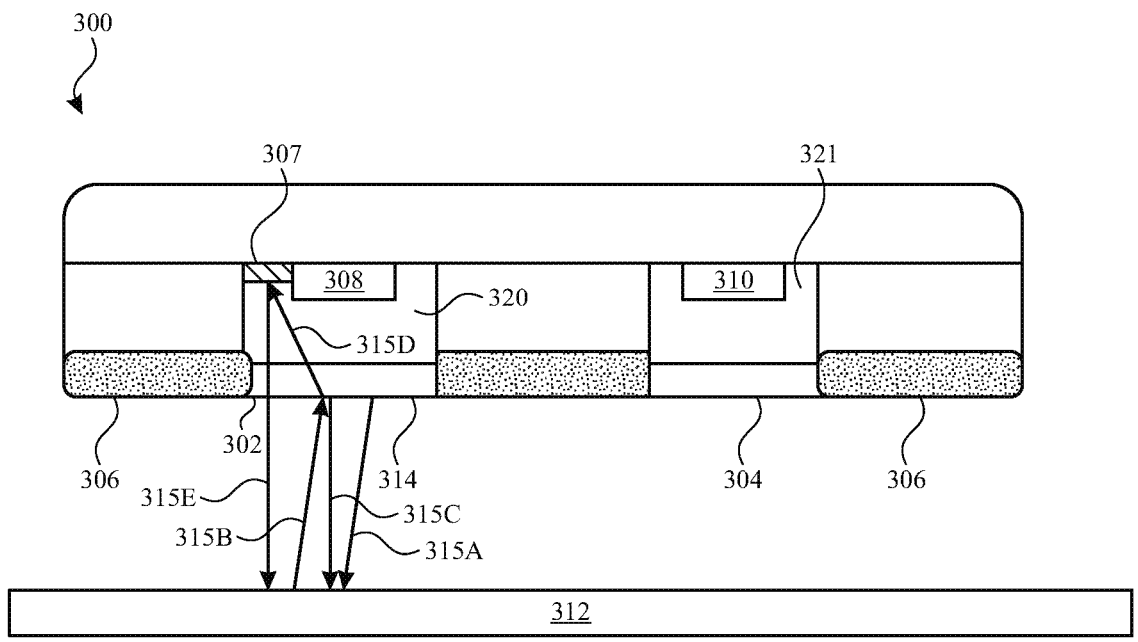
FIG. 3 illustrates an exemplary electronic device including retroreflectors located both within the light emitter cavity and disposed within the window according to examples of the disclosure.

In some examples, the electronic device can include retroreflectors located both within the light emitter cavity and disposed within the window. FIG. 3 illustrates an exemplary electronic device including retroreflectors located both within the light emitter cavity and disposed within the window according to examples of the disclosure. Housing 300 can include window 302 coupled to cavity 320 and window 304 coupled to cavity 321. Cavity 320 can include light emitter 308, and cavity 321 can include photodetector 310. Housing 300 and back surface 306 can include an opaque material configured to block the transmission of light. Light 315A emitted by light emitter 308 can pass through window 302 and can travel toward body tissue 312. In some instances, light 315A can interact with tissue and can reflect back, passing through window 304, and entering into cavity 321 to be collected by photodetector 310.

In some instances, light 315A can reflect back towards cavity 320 as light 315B. Light 315B may be incident on window 302, which can include a retroreflector 314. Retroreflector 314 can be configured to reflect light 315B back, as light 315C, along a direction that is parallel (or nearly parallel) to, but opposite from the direction of light emitted by light emitter 308, irrespective of the angle of incidence. One of skilled in the art would understand that nearly parallel includes, for example, a 5-10% deviation from parallel.

In some examples, housing 300 can further include one or more retroreflectors 307 located within cavity 320. In some instances, light 315A may reflect back and pass through window 302 as light 315D. Retroreflector 307 can be configured to reflect light 315D back, as light 315E, along a direction that is parallel (or nearly parallel) to, but opposite from the direction of light emitted by light emitter 308, irrespective of the angle of incidence. One of skilled in the art would understand that nearly parallel includes, for example, a 5-10% deviation from parallel. In some examples, retroreflector 307 can be configured to reflect light (not shown) that has not passed through window 302 out of cavity 320. Examples of the disclosure can include one or more reflectors (e.g., reflector 107 illustrated in FIG. 1D) located in cavity 321.

Figure 4A:
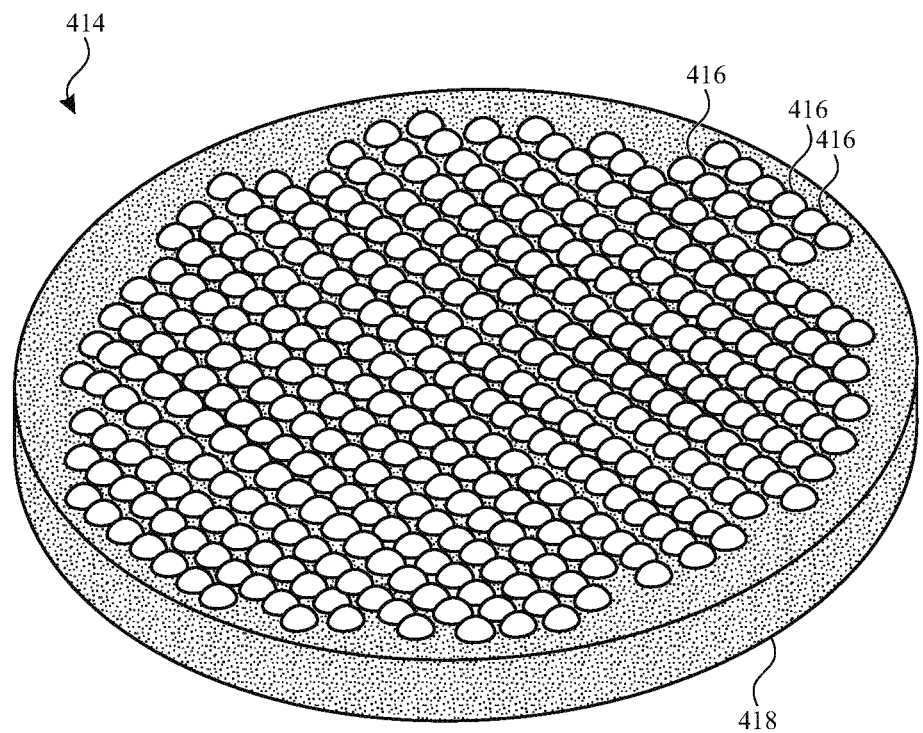
FIGS. 4A-4B illustrate perspective and cross-sectional views of an exemplary retroreflector including hemispheres according to examples of the disclosure.
Figure 4B:
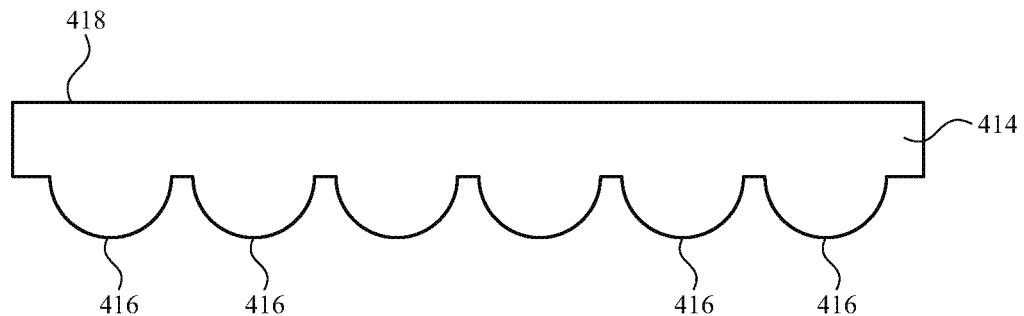

FIGS. 4A-4B illustrate perspective and cross-sectional views of an exemplary retroreflector including hemispheres according to examples of the disclosure. Substrate 414 may comprise a plurality of geometric elements in the form of hemispheres 416 that protrude back toward tissue (e.g., tissue 212 illustrated in FIG. 2). Surface 418 can face one or more light emitters (e.g., light emitter 108 illustrated in FIG. 1B or light emitter 208 illustrated in FIG. 2).

Figure 4C:
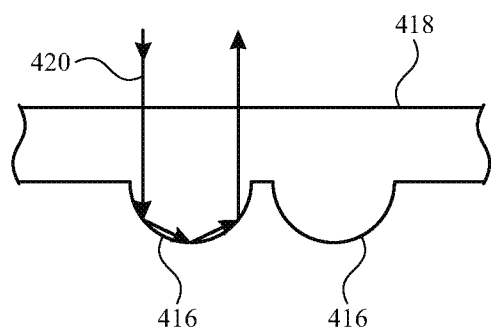
FIG. 4C illustrates a magnified view of the hemispheres included in an exemplary retroreflector according to examples of the disclosure.

FIG. 4C illustrates a magnified view of the hemispheres included in an exemplary retroreflector according to examples of the disclosure. Hemispheres 416 can reflect reflected and/or scattered light 220 back toward body tissue (located closer to surface 418 than the protrusions of hemispheres 416).

Figure 4D:
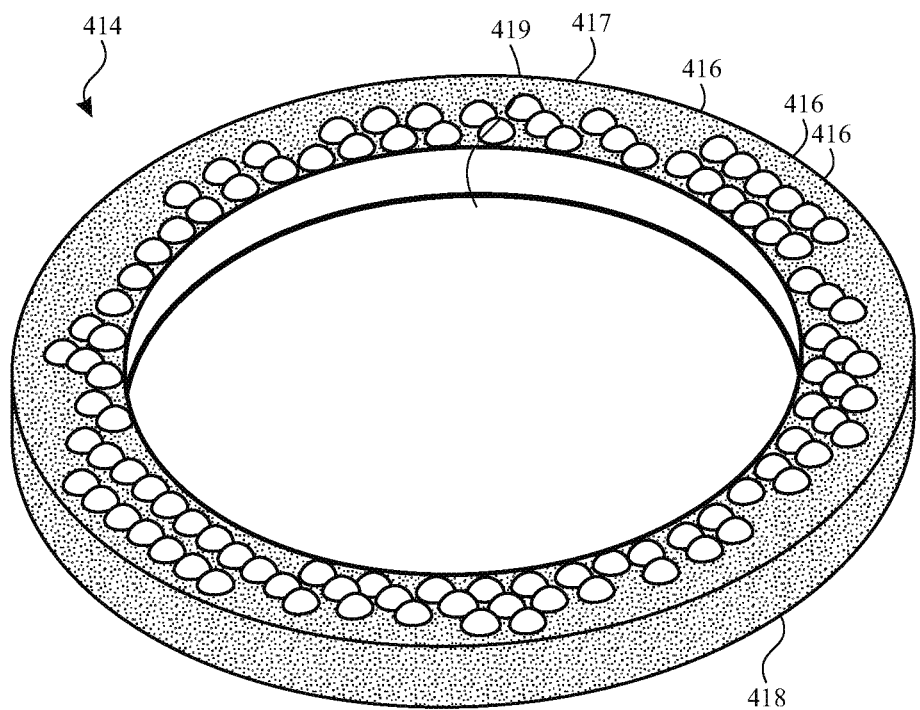
FIG. 4D illustrates a perspective view of an exemplary retroreflector including geometric elements disposed on the outer perimeter according to examples of the disclosure.

Retroreflector 414 can be formed within and/or disposed (e.g., a separate coating layer) on the substrate. In some examples, the geometric elements can be located through the substrate, as shown in FIG. 4A. In some examples, the geometric elements can be located in one or more areas of the substrate and excluded from other areas of the substrate. For example, the geometric elements can be disposed on the outer perimeter of the retroreflector, as illustrated in FIG. 4D. Substrate 418 can include regions 417 and 419, where region 417 can include hemispheres 416 and region 419 can exclude hemispheres or any geometric elements. In some examples, region 419 can include a different type of geometric element than region 417.

In some examples, the substrate can be configured as a window, where region 419 can be transparent without retroreflective properties and configured to allow light to pass through. Region 417 can be configured with retroreflective properties by including one or more geometric elements. Although FIG. 4D illustrates a circular substrate with geometric elements patterned around the perimeter of the substrate, examples of the disclosure can include any shape and size substrate. Additionally, examples of the disclosure can include any pattern, such as a grid or mesh of geometric elements.

Figure 5A:
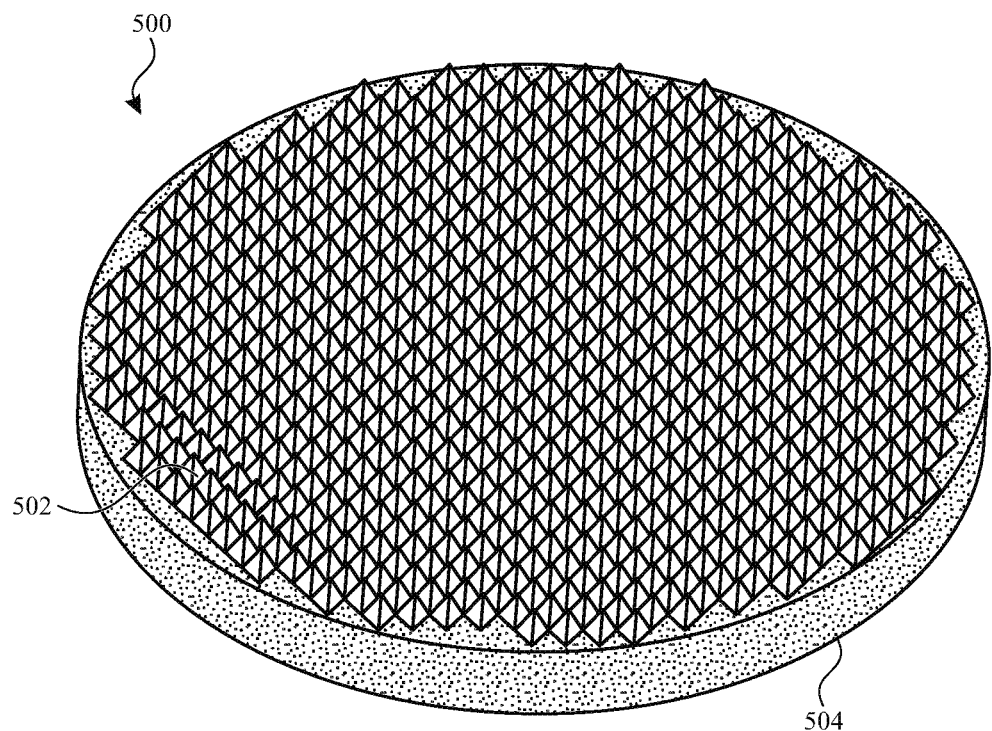
FIGS. 5A-5B illustrate perspective and magnified cross-sectional views of an exemplary retroreflector having corner cube geometric elements according to examples of the disclosure.
Figure 5B:
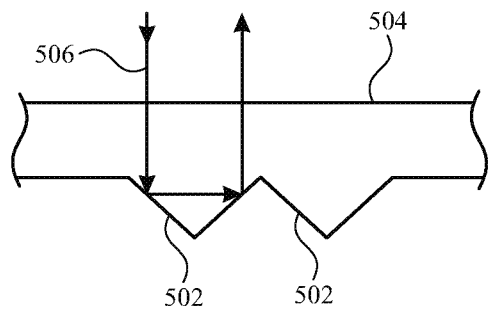

In another variation, as shown in the top view illustrated in FIG. 5A, the substrate 300 may comprise geometric elements in the form of corner cubes 502. Surface 504 can be configured to face body tissue (e.g., tissue 212 illustrated in FIG. 2A). In the magnified cross-sectional view provided in FIG. 5B, corner cube 502 can reflect reflected and/or scattered light 506 back towards body tissue. Although hemispheres and corner cubes are shown in the figures, it is understood that other geometric elements capable of retroreflecting light can be employed.

The retroreflectors disclosed herein may be implemented in any electronic device in which the collection of reflected and/or scattered light is useful. For example, the retroreflectors may be used in PPG sensor systems and proximity sensor systems.

Memory of electronic device can be a non-transitory computer-readable storage medium, for storing computer-executable instructions, which, when executed by one or more computer processors, for example, can cause the computer processors to perform the algorithms for processing the signals, e.g., the PPG signals, or for generating proximity curves. The computer-executable instructions can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. For purposes of this document, a "non-transitory computer-readable storage medium" can be any medium that can tangibly contain or store computer-executable instructions for use by or in connection with the instruction execution system, apparatus, or device. The non-transitory computer-readable storage medium can include, but is not limited to, magnetic, optical, and/or semiconductor storages. An example of such storage includes persistent solid-state memory such as flash, solid-state drives, and the like. A processor (not shown) may be included in the housing that is configured to run various algorithms based on the signals collected by the photodetector. The processor can be a single-chip processor or can be implemented with multiple components.

The electronic devices may also include a power system for powering the various components. The power system may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Methods for enhancing collection of a scattered signal are further disclosed herein. The methods generally include the steps of attaching a electronic device to a body area of a user, the electronic device comprising a housing having a back surface; and a light emitter unit and a photodetector within the housing, the light emitter unit comprising a light emitter and a retroreflector, where the retroreflector comprises a substrate having a reflective surface; illuminating the body area with light from the light emitter; and redirecting reflected and/or scattered light out of the housing using the retroreflector. The retroreflector may redirect the reflected and/or scattered light to a body tissue for potential reflection to a photodetector.

Attachment of the electronic device to a user can be accomplished in various ways. For example, the electronic device can be secured to a user by attachment mechanisms such as, but not limited to, arm bands, headbands, watch straps, and belts, as previously stated. Other types of attachment mechanisms may include bands that may be secured to the user through the use of hooks and loops (e.g., Velcro), a clasp, and/or a band having memory of its shape, e.g., through the use of a spring metal band.

In some variations, reflected and/or scattered light is redirected using a retroreflector including a substrate having an inner surface, an outer surface, and a geometric element. The geometric element may comprise a corner cube (illustrated in FIG. 5A-5B), a cat's eye, or a hemisphere (illustrated in FIGS. 4A-4C). Alternatively, the geometric element may comprise a prism. The geometric element may be integrally formed on the outer surface of the substrate or on the inner surface of the substrate. In some instances, the geometric element is provided in a coating that is layered on the substrate.

Whether integrally formed on a surface of the substrate or layered in a coating thereon, the geometric elements may be disposed on the entire inner surface or entire outer surface of the substrate, disposed on a portion of the inner surface or on a portion of the outer surface of the substrate, or configured as a pattern on the inner surface or on the outer surface of the substrate. For example, patterning may include placing the geometric elements on a discrete portion(s) of the inner surface or on a discrete portion(s) of the outer surface of the substrate. Patterning may further include, e.g., providing the geometric elements on a perimeter or central area of the substrate, in one or more strips on the substrate, or symmetrically or asymmetrically on the substrate. In some variations, the same geometric element is disposed on the substrate. In other variations, different or combinations of geometric elements are disposed on the substrate.

Although the reflective surfaces have been described as being retroreflective, it is understood that in some variations the reflective surface may comprise a reflective ink or film, or other materials that are specularly reflective or diffusely reflective. Similar to the geometric elements described above, the reflective surface can be disposed on the substrate in any suitable fashion that enables enhanced collection of light. For example, the reflective surface may be disposed on, or include, the entire outer surface of the substrate, or a portion of the outer surface of the substrate. In one variation, the reflective surface is configured as a pattern on the outer surface of the substrate. For example, patterning may include placing the reflective material on a discrete portion(s) of the outer surface of the substrate. Patterning may further include, e.g., providing the reflective material on a perimeter or central area of the substrate, in one or more strips on the substrate, or symmetrically or asymmetrically on the substrate. In some variations, the same reflective material is disposed on the substrate. In other variations, different or combinations of reflective materials are disposed on the substrate.

Figure 1B:
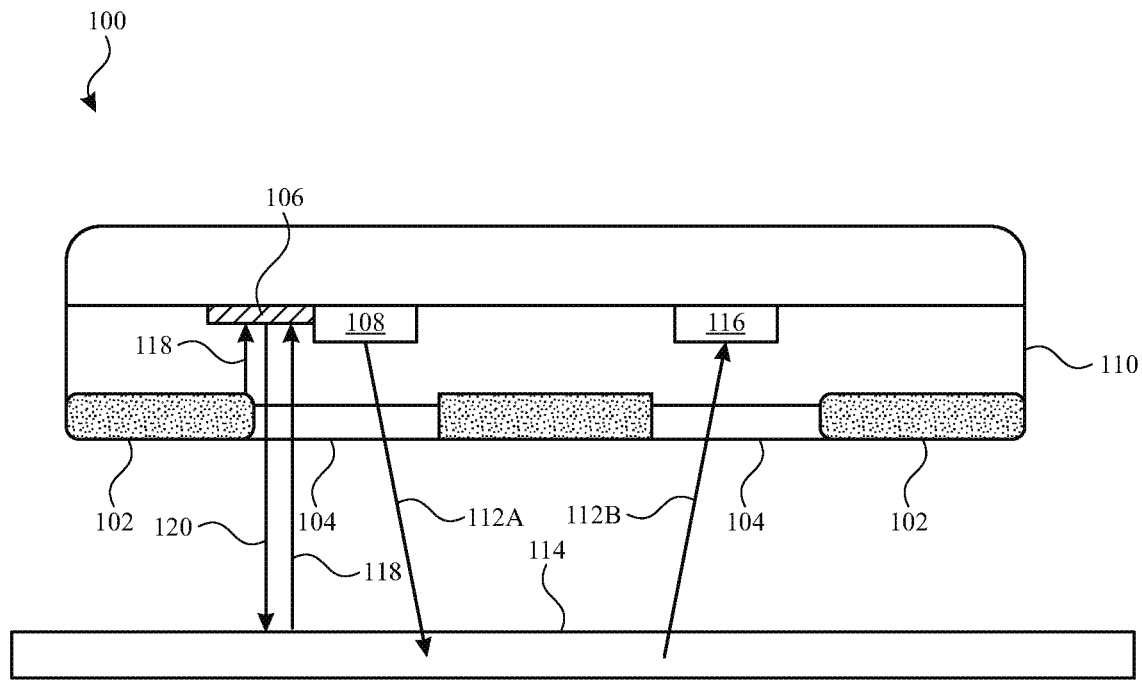
FIG. 1B illustrates a cross-sectional view of the housing and openings shown in FIG. 1A taken along line A-A, and an exemplary retroreflector disposed within the housing according to examples of the disclosure.
Figure 1C:
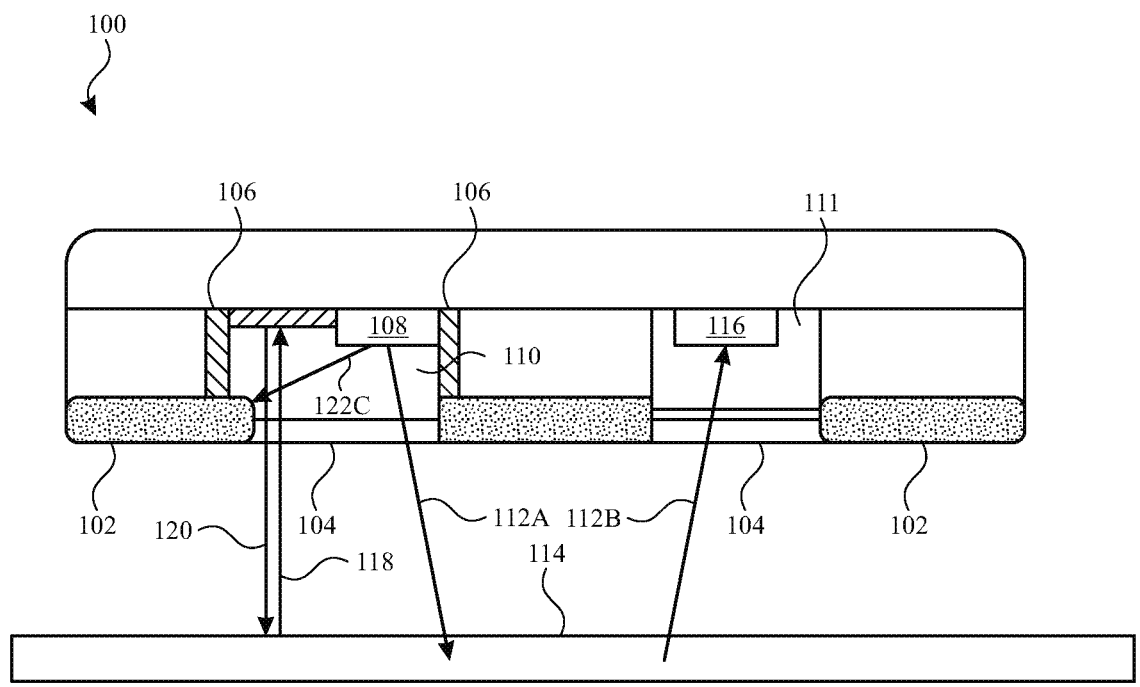
FIG. 1C illustrates an exemplary electronic device including multiple retroreflectors located within the light emitter cavity according to examples of the disclosure.
Figure 1D:
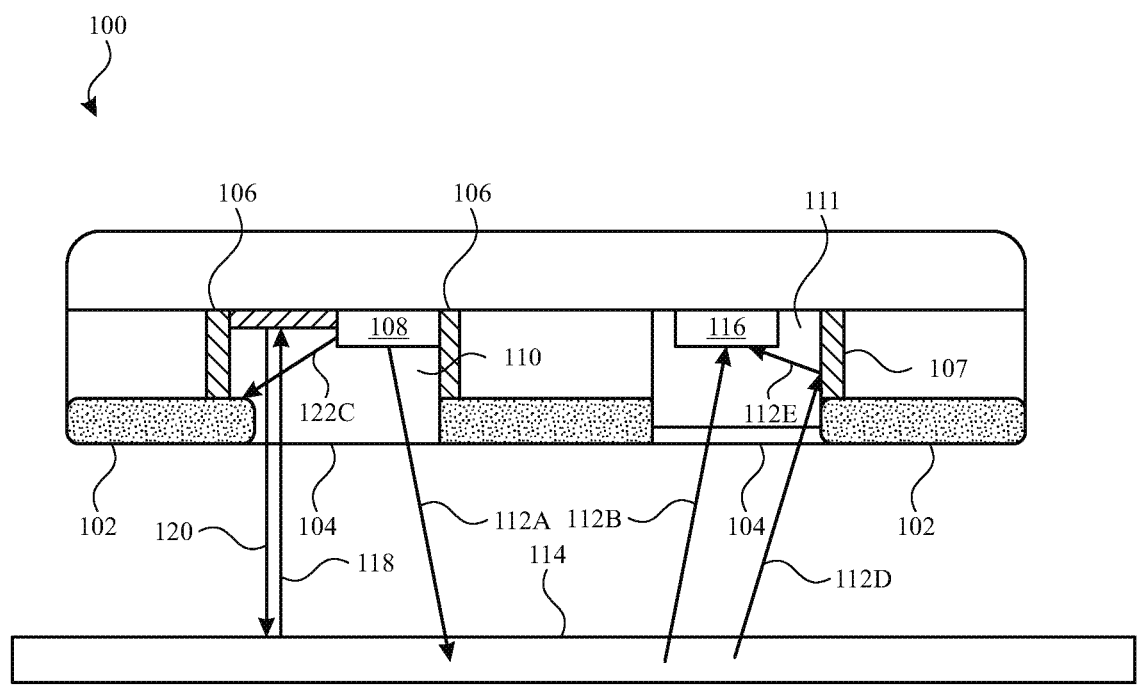
FIG. 1D illustrates an exemplary electronic device including retroreflectors and Lambertian reflectors according to examples of the disclosure.

When a retroreflector is employed, the reflected and/or scattered light can be redirected out of the housing, as shown in FIG. 1B. Light can also be redirected from the outer surface of the substrate, as illustrated in FIG. 2. The electronic device may be any device suitable for collection of signals and attachment to a body area of a user, e.g., a wrist of a user. In one variation, the electronic device comprises a wristwatch.

Enhancing the collection of light may help to improve detection of physiological signals, e.g., PPG signals, improve generation of proximity curves, as well as save battery life of the electronic device. For example, improved proximity curves (i.e., having a shape closer to an ideal proximity curve), can be generated with sensors having retroreflectors including geometric elements (e.g., hemispheres and corner cubes) provided in various configurations such as on the entire outside surface of the substrate or discrete portions thereof (e.g., in one quadrant of the substrate, in strips, etc.).

A processor included in the electronic device will generally be configured to execute algorithms for processing the collected signals to generate proximity curves, z distances, and physiological data, etc., and control the reception and manipulation of input and output data between components of electronic device.

In some variations, the processor together with an operating system can operate to execute computer code and produce and use data. The computer code and data can reside within a program storage block that can be operatively coupled to the processor. The program storage block can generally provide a place to hold data that is being used by the operating system. The program storage block can be any non-transitory computer-readable storage medium, and can store, for example, history and/or pattern data relating to proximity curves measured by one or more photodetectors.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

The present disclosure recognizes that personal information data, including biometric data, in the present technology, can be used to the benefit of users. For example, the use of biometric authentication data can be used for convenient access to device features without the use of passwords. In other examples, user biometric data is collected for providing users with feedback about their health or fitness levels. Further, other uses for personal information data, including biometric data, which benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data, including biometric data. That is, the present disclosure contemplates that hardware and/or software elements can be provided to prevent or block access to such personal information data. For example, in the case of biometric authentication methods, the present technology can be configured to allow users to optionally bypass biometric authentication steps by providing secure information such as passwords, personal identification numbers (PINS), touch gestures, or other authentication methods, alone or in combination, known to those of skill in the art. In another example, users can select to remove, disable, or restrict access to certain health-related applications collecting users' personal health or fitness data.

The invention claimed is:

1. An electronic device comprising:
 a housing including an outer surface, a first cavity, and a second cavity;
 one or more light emitters located in the first cavity and optically coupled to at least one first window;
 one or more photodetectors located in the second cavity and optically coupled to at least one second window; and
 one or more retroreflectors optically coupled to the one or more light emitters, wherein when the electronic device is placed against a tissue of a user, the one or more retroreflectors reflect incident light back to the tissue and in a direction that is parallel or nearly parallel to but opposite from the incident light.

2. The electronic device of claim 1, wherein the one or more retroreflectors include a substrate and a reflective surface disposed on a surface of the substrate.

3. The electronic device of claim 2, wherein the substrate is transparent.

4. The electronic device of claim 1, wherein at least one of the one or more retroreflectors is located adjacent to at least one of the one or more light emitters.

5. The electronic device of claim 1, wherein the one or more retroreflectors include a substrate and a reflective surface disposed in a pattern on the substrate.

6. The electronic device of claim 1, wherein the one or more light emitters are located on a first surface in the first cavity and at least one of the one or more retroreflectors is disposed on a second surface in the first cavity, the second surface different from the first surface.

7. The electronic device of claim 1, wherein the one or more retroreflectors are disposed on the outer surface of the housing.

8. The electronic device of claim 1, wherein the one or more retroreflectors are disposed on the at least one first window.

9. The electronic device of claim 1, further comprising:
 one or more reflectors optically coupled to the one or more photodetectors, the one or more reflectors configured to reflect light into the second cavity.

10. The electronic device of claim 8, wherein the one or more reflectors include a Lambertian reflector.

11. The electronic device of claim 1, wherein at least one of the one or more retroreflectors is located in the first cavity and at least another of the one or more retroreflectors is located on one or more of the outer surface of the housing and the at least one first window.

12. The electronic device of claim 1, wherein the one or more retroreflectors include a plurality of geometric elements, the plurality of geometric elements including one or more of hemispheric structures, prisms, corner cubes, and cat's eye structures.

13. The electronic device of claim 1, further comprising:
 logic configured to:
 receive one or more signals from the one or more photodetectors, and determine one or more physiological information from the one or more signals.

14. The electronic device of claim 1, wherein the electronic device is a wearable device.

15. A method for collecting light using an electronic device, the method comprising:
 locating one or more light emitters in a first cavity included in a housing;
 emitting a first light using the one or more light emitters;
 placing the electronic device against a tissue of a user reflecting a second light using one or more retroreflectors when the electronic device is placed against the tissue of the user, the one or more retroreflectors reflecting incident light back to the tissue and in a direction that is parallel or nearly parallel to but opposite from the incident light;
 locating one or more photodetectors in a second cavity included in the housing; and detecting the light reflected by the one or more retroreflectors using the one or more photodetectors.

16. The method of claim 15, further comprising:
 allowing the light reflected by the one or more retroreflectors to pass through at least one first window, the at least one first window coupled to the first cavity; and
 allowing the light reflected by the one or more retroreflectors to pass through at least one second window, the at least one second window coupled to the second cavity.

17. The method of claim 15, wherein the opposite direction is towards the one or more photodetectors and the one or more reflectors are located in the second cavity.

18. The method of claim 15, further comprising:
 receiving one or more signals from the one or more photodetectors; and
 determining one or more physiological information from the one or more signals.

19. A method for forming an electronic device, the method comprising:
provide a housing, the housing including an outer surface, a first cavity, and a second cavity;
locating one or more light emitters in the first cavity;
attaching one or more first windows to the first cavity;
locating one or more photodetectors in the second cavity;
attaching one or more second windows to the second cavity; and
locating one or more retroreflectors such that when the electronic device is placed against a tissue of a user, the one or more retroreflectors reflect incident light back to the tissue and in a direction that is parallel or nearly parallel to, but opposite to, the direction of the incident light, the one or more retroreflectors optically coupled to the one or more light emitters.

20. The method of claim 19, further comprising:
locating one or more reflectors, the one or more reflectors optically coupled to the one or more photodetectors.

* * * * *